(12) United States Patent
Mannar et al.

(10) Patent No.: US 7,885,384 B2
(45) Date of Patent: Feb. 8, 2011

(54) SYSTEM AND METHOD TO MANAGE MAINTENANCE OF A RADIOLOGICAL IMAGING SYSTEM

(75) Inventors: Kamal Mannar, Waukesha, WI (US); Yibin Zheng, Hartland, WI (US)

(73) Assignee: General Electric Company, Schenectady, NY (US)

(*) Notice: Subject to any disclaimer, the term of this patent is extended or adjusted under 35 U.S.C. 154(b) by 0 days.

(21) Appl. No.: 12/359,408

(22) Filed: Jan. 26, 2009

(65) Prior Publication Data
US 2010/0189227 A1  Jul. 29, 2010

(51) Int. Cl.
H05G 1/54  (2006.01)
(52) U.S. Cl. ...................... 378/118; 378/207
(58) Field of Classification Search ............... 378/207, 378/101, 117, 118
See application file for complete search history.

(56) References Cited

U.S. PATENT DOCUMENTS

| | | | |
|---|---|---|---|
| 5,668,850 A | 9/1997 | Abdel-Malek | 378/210 |
| 6,212,256 B1 | 4/2001 | Miesbauer et al. | 378/118 |
| 6,351,517 B1 | 2/2002 | Guru et al. | 378/91 |
| 6,453,009 B2 | 9/2002 | Berezowitz et al. | 378/118 |
| 6,847,918 B2 | 1/2005 | Loecher | 702/184 |
| 6,912,481 B2 | 6/2005 | Breunissen et al. | 702/184 |
| 7,299,162 B2 | 11/2007 | Loecher et al. | 703/2 |
| 2007/0189463 A1* | 8/2007 | Deuringer et al. | 378/207 |
| 2009/0281867 A1 | 11/2009 | Sievenpiper et al. | 705/10 |

* cited by examiner

Primary Examiner—Courtney Thomas

(57) ABSTRACT

A system and method to predict a failure of an imaging system that includes a radiation source having an x-ray tube assembly is provided. The system includes a storage medium having a plurality of programmable storage instructions to instruct a processor to perform the steps of acquiring an age of the x-ray tube assembly, calculating a baseline probability of a survivability of the tube assembly for a remaining time period dependent on the age of the tube assembly, acquiring measurement of at least one operating parameter of the x-ray tube assembly, and automatically changing the baseline probability of a survivability of the imaging system for the remaining time period in response to the measurement of the at least one operating parameter of the x-ray tube assembly.

18 Claims, 8 Drawing Sheets

SYSTEM AND METHOD TO MANAGE MAINTENANCE OF A RADIOLOGICAL IMAGING SYSTEM

BACKGROUND

The subject herein generally relates to a system and method to perform maintenance on a radiological imaging system, and more specifically, system and method to predict failure of an X-ray tube of the radiological imaging system.

A leading cause of unplanned shutdown of radiological imaging systems (e.g., X-ray, Computed Tomography (CT)) includes failure of an X-ray tube installed therein. Tube failure can be highly disruptive to the delivery of healthcare to patients, as well as the operation and revenue generation of the radiological imaging systems.

The above-mentioned problem can be addressed by the subject matter described herein in the following description.

BRIEF SUMMARY

The system and method of the subject matter described herein provide enhanced prediction of a survivability for a remaining time period of an imaging system having a radiation source with an x-ray tube assembly. The system and method can increase the lead time for service operations to schedule shipment and installation of the replacement tube with reduced unplanned downtime.

According to one embodiment, a method to predict a failure of an imaging system that includes a x-ray tube assembly as a radiation source is provided. The method includes the steps of acquiring an age of the x-ray tube assembly; calculating a baseline probability of a survivability of the tube assembly for a remaining time period independent of a usage of the tube assembly; acquiring measurement of at least one operating parameter of the x-ray tube assembly; and automatically changing the probability of a survivability of the x-ray tube assembly in response to the measurement of the at least one operating parameter of the x-ray tube assembly.

According to another embodiment, a system to predict a failure of an imaging system that includes a radiation source having an x-ray tube assembly is provided. The system comprises a storage medium having a plurality of programmable storage instructions; and a processor in communication with the imaging system, the plurality of program instructions to instruct the processor to perform the steps of: acquiring an age of the x-ray tube assembly; calculating a baseline probability of a survivability of the tube assembly for a remaining time period dependent on the age of the tube assembly; acquiring measurement of at least one operating parameter of the x-ray tube assembly; and automatically changing the baseline probability of a survivability of the imaging system for the remaining time period in response to the measurement of the at least one operating parameter of the x-ray tube assembly.

Various other features, objects, and advantages of the invention will be made apparent to those skilled in the art from the accompanying drawings and detailed description thereof.

DETAILED DESCRIPTION

In the following detailed description, reference is made to the accompanying drawings that form a part hereof, and in which is shown by way of illustration specific embodiments that may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken as limiting the scope of the invention.

Figure 1:
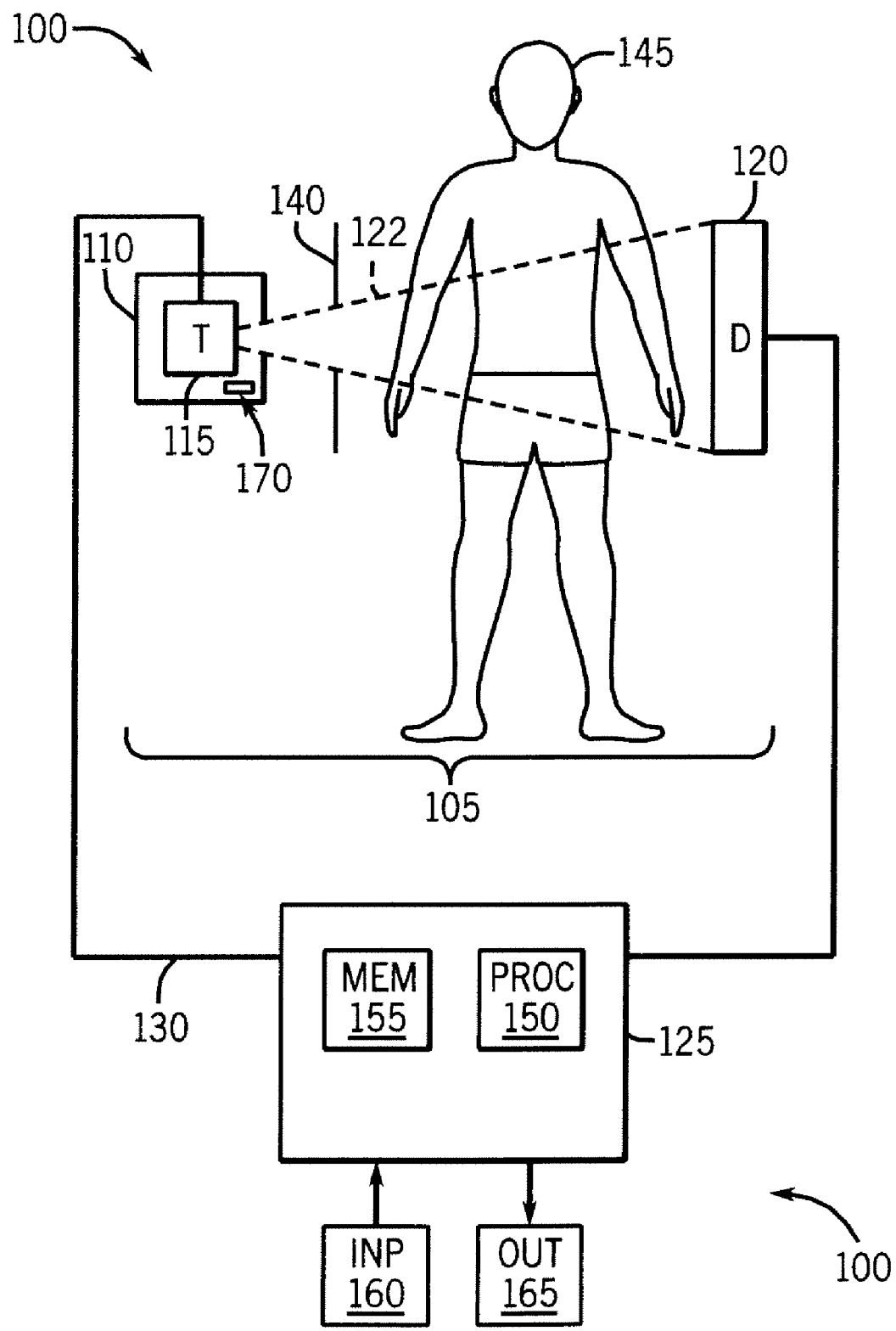
FIG. 1 includes a diagrammatical representation of an imaging system in combination with an embodiment of a management system of the subject matter described herein, the imaging system incorporating an x-ray tube as a source of radiation.

FIG. 1 illustrates an embodiment of a management system 100 operable to manage maintenance on an imaging system 105 employing a radiation source 110. The embodiment of the radiation source 110 of the imaging system 105 can comprise x-ray tube assembly 115 (also referred to as "the tube assembly 115"). The illustrated embodiment of the imaging system 105 is of a digital x-ray imaging system that includes a detector 120 operable to detect attenuation of a stream of radiation 122 transmitted from the tube 115. Yet, the type (e.g., systems employing x-ray tubes such as conventional x-ray systems, CT systems, tissue ablation or cauterization system, sterilizing system, x-ray crystallography system to reveal a nature of a crystal lattice, x-ray microscopic analysis system to produce images of small objects, industrial radiography systems to inspect industrial parts or welds, airport security systems, etc.) of x-ray system 105 can vary.

The embodiment of the radiation source 110 can receive power and control signals from a controller 125. The controller 125 can convert alternating current power to direct current power and can apply controlled pulses of DC power to the tube 115 to induce emissions of x-ray radiation for examination purposes. Moreover, the controller 125 can monitor a range of operating conditions or parameters of the tube 115, as described in more detail below. A set of conductors 130 can convey power and control signals from the controller 125 to the tube 115.

Under the command of the controller 125, the tube 115 of the radiation source 110 produces the stream of radiation 122. The stream of radiation 122 can be directed through a collimator 140 and passes through a subject 145, such as a human patient. The detector 120 can measure and convert attenuation of the stream of radiation 122 through the subject 145 to image data. The detector 120 can convey the image data as signals to the controller 125 for processing.

The controller 125 can provide control signals to regulating scanning of the detector 120. Moreover, the controller 125 may perform additional signal processing or signal filtering functions. The controller 125 can also acquire the image data and performs further processing and filtration functions. In particular, the controller 125 can derives discrete data from the acquired signals and reconstructs useful images from the data.

The controller 125 can include a processor 150 generally configured to execute program instructions stored in the memory 155. Although the memory 155 and processor 150 are shown at the controller 125, it should be understood that the memory 155 or processor 150 can comprise remote portions.

The controller 125 can also be in communication with an input device 160 and an output device 165. Examples of the input device 160 include a keyboard, an touch screen or graphic interface, mouse, toggle switches, etc. Example of the output device 165 can include monitors, touch-screens or graphic interfaces, kiosks, dashboards, etc. The input and output devices 160 and 165 can be combined as an operator interface in communication to exchange configuration data, examination requests, and so forth with the controller 125. The operator interface can include an operator workstation that permits clinicians or radiologists to request and control specific examinations, review data log files, view reconstructed images, and output reconstructed images on a tangible medium, such as photographic film.

The controller 125 can store the image data in the memory 150. The memory 150 may also store configuration parameters, data log files, and so forth. The controller 125 can provide signals to control emission of x-ray radiation from the radiation source 110. The controller 125 may also include communication circuitry (wired or wireless) for providing interactive data exchange with remote computer stations, such as a remote service center as described more fully below.

The system 100 may also include sensors 170 to detect specific operating parameters of the radiation source 110, such as (but not limited to) temperature, current, voltage, and vibration, values of which may also be stored and analyzed as described below.

As noted above, the foregoing description of the system 100 is directed to digital x-ray imaging. Of course, the system 100 can include other control and interface circuitry on other scanner types, such as conventional x-ray systems, CT imaging systems, and so forth. In general, however, such system 100 can include the controller 125 to regulate emission of x-ray radiation for examination or calibration purposes. Moreover, for implementation of the technique described herein, such system 100 can include capabilities to monitor or track performance of the tube assembly 115 during such examination or calibration sequences such that parameters considered as leading indicators of tube failure may be acquired, stored and analyzed.

Figure 2:
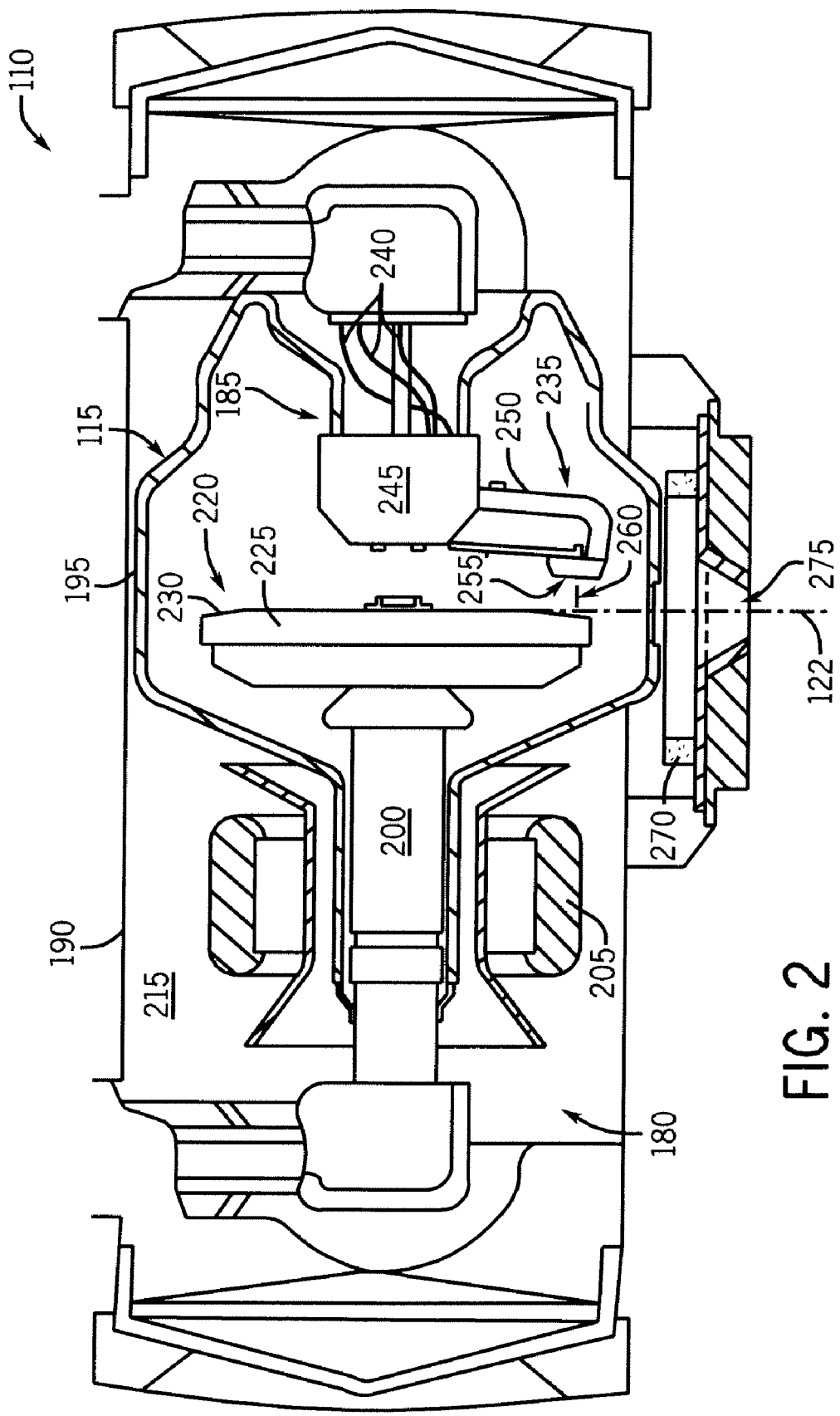
FIG. 2 includes a detailed diagram of an embodiment of an x-ray tube of the type incorporated in the imaging system of FIG. 1.

FIG. 2 illustrates an embodiment of the radiation source 110, including the x-ray tube assembly 115. The embodiment of the x-ray tube assembly 115 can include an anode assembly 180 and a cathode assembly 185. The anode and cathode assemblies 180 and 185 can be positioned within a casing 190 which may be made of aluminum and lined with lead material composition. The tube assembly 115 can be supported from the anode and cathode assemblies 180 and 185. The tube assembly 115 can further include an envelope 195, with a rotor 200 positioned therein generally adjacent to the anode assembly 185. A stator 205 can at least partially surround the rotor 200. The casing 190 can be filled with a cooling medium 215 such as oil around the envelope 195. The cooling medium 215 can also enhance high voltage insulation.

The anode assembly 180 can be positioned within the envelope 195. An embodiment of the anode assembly 180 includes an anode 220 having a front portion comprising a target disc 225. The target disc 225 can include a target or focal surface 230. The cathode assembly 185 can include a cathode 235 coupled to a series of electrical leads 240. The cathode 235 can include a central shell 245 from which a mask 250 extends. The mask 250 can enclose and conduct the leads 240 to a cathode cup 255. The cathode cup 255 can serve as an electrostatic lens that focuses electrons emitted from a heated filament (not shown) supported by the cup 255.

Control signals conveyed from the controller 125 via the leads 240 to the cathode 235 can regulate or control energizing of the cathode filaments (not shown) within the cup 240 so as to produce an electron beam 260. The beam 260 can be directed to strike the focal surface 230 of the anode target disc 225 so as to cause or generate the stream of radiation 122 therefrom to be transmitted from the x-ray tube assembly 115. A deflection coil 270 can produce a magnetic field to control the direction and orientation of the stream of radiation 122. The controller 125 can control the intensity and direction of magnetic field produced by the deflection coil 270. The stream of radiation 122 can exit the radiation source 110 through an aperture 275 in the casing 190 provided for this purpose.

Stream of x-ray radiation 122 can be produced in the x-ray tube assembly 115 when, in a vacuum, electrons are released and accelerated by the application of high voltages and currents to the cathode assembly 185 and then abruptly intercepted by the anode target disc 225. The voltage difference between the cathode 235 and anode 220 may range from tens of thousands of volts to in excess of hundreds of thousands of volts. Moreover, the anode target disc 225 may be rotated such that electron beams are constantly striking a different point on the target or focal surface 230. Depending upon the construction of the tube assembly 115, the desired radiation may be emitted by substances such as radium or artificial radiotropics, as well as electrons, neutrons and other high speed particles. Within the envelope 195 of tube assembly 115, a vacuum on the order of $10^{-5}$ to about $10^{-9}$ torr at room temperature can be maintained to permit transmission of the electron beam 260 between the anode 220 and cathode 235.

As noted above, in addition to providing power and control signals for operation of the radiation source 110 or tube assembly 115, the controller 125 can track or acquire feedback or operating parameters of the radiation source 110 or tube assembly 115. Certain of these parameters to be described later can be considered as predictive of future failure or survivability of the radiation source 110 or tube assembly 115. Such parameters may be measured via the sensors 170 (see FIG. 1), and can also be available from the characteristics of the control and power signals applied to the radiation source or tube assembly 115.

While the electron beam 260 is created in a vacuum, particulates or contaminants may be present in the tube assembly 115. Such particulates may be introduced in the tube assembly 115 via leaks, degradation of components, decomposition of components, and so forth. When the electron beam 260 impacts such particulate matter, the electron beam 260 may continue toward the anode target disk 225 or the electron beam 260 may be deflected from the target disk 225. Each above-described incident of the particulate with the electron beam can create anomalies (e.g., current anomalies) in the signals exchanged between the tube assembly 115 and the controller 125. An example of such anomaly is an anode high current discharge, also referred to as an anode overcurrent event, associated with the particulate encountering the electron beam and the beam continuing along its path to impact the anode target disk 225. Another example of such anomaly is a "spit" event, associated where the particulate may divert the electron beam from the anode target disk 225 to cause the current discharge event. The controller 125 can receive feedback of measurement of current at the anode target disk 225 and via comparators and other circuitry or software modules can detect or track occurrence of the anomalies, as well as distinguish between anode overcurrent events and spits. The controller 125 can record and save detection of occurrence of such anomaly events at the memory 155.

The controller 125 can also be configured to acquired data from one or more sensors 170 or feedback from components of the x-ray tube assembly 115, radiation source 110 or imaging system 105 to track other failure modes for tube assemblies, including rotor failure and filament failure. The anode of the tube assembly 115 can continuously rotate to provide fresh material under the electron beam 122 by vacuum compatible bearings. The rotor control function can provide three phase motor power to the rotating anode of the tube assembly 115. The high stress environment of heat and mechanical load can increase likelihood of an anode rotor bearing failure. The controller 125 can acquire data (e.g., from the rotor control) of increased amount of current from the motor control during acceleration and run states relative to thresholds, which can be determinative of an increased likelihood or lower survivability due to a failure condition of the anode rotor bearing. This above-described acquired data of failure condition of the anode rotor bearing can be logged at the memory 155.

Similar to rotor failure; filament failure can another significant failure mode. The tungsten alloy filament can be electrically heated in the cathode structure to very high temperatures to create an electron cloud. Open filament circuit is one of the common failure modes. The mA Filament Control Board monitors the voltage at the output of the filament inverter. The controller can detect or receive data of an improper voltage via the filament control board, and log the anomaly at the memory 155.

In addition to recording the actual number of anode overcurrent events and spits, the controller 125 can track measurement of additional parameters. For example, the controller 125 can detect and record a number of spits per day of operation. Moreover, the controller 125 can detect interruption of current to the tube assembly 115 upon the occurrence of the spit event, and the subsequently reapplication of current during an examination sequence. Such events can recorded by the controller 125 and logged in the memory 150 for each day of operation. The controller 125 can receive instructions or be preset to detect a maximum "spit rate" limit (e.g., in terms of spits per unit time). If the controller 125 calculates that the measured spit rate is greater than the preset spit rate limit, the controller 125 can automatically abort or otherwise stop a scan or examination. For example, in one embodiment, if the controller 125 detects measures the spit rate to be over 32 spits/second, the controller 125 can automatically abort or otherwise cause a present examination scan to be aborted. Such events can be termed "spit rate exceeded" errors (SREs). The controller 125 can also track a number of SREs per day and store in the memory 150. The controller 125 also records events when rotor drive control circuit detects an anomaly, for example, if the rotor cannot be brought up to speed in a prescribed time, or an overcurrent in acceleration, etc. The controller 125 also monitors the filament voltage and current and records events when these parameters are out of bound indicating a possible open filament.

A first baseline model or algorithm comprising parameters that are dependent or associated with occurrence of event codes can be integrated with a second model or algorithm comprising tracked parameters associated with usage of the radiation source 110 or tube assembly 115 to create a composite algorithm to predict a likelihood or failure of the tube assembly 115. The rate of occurrence of anode overcurrent events and SREs, as well as rotor and filament events can be applied to this composite algorithm to predict the likelihood of failure or survivability of the tube assembly 115. An example of creating the composite algorithm can be according to a technique as described below.

Figure 3:
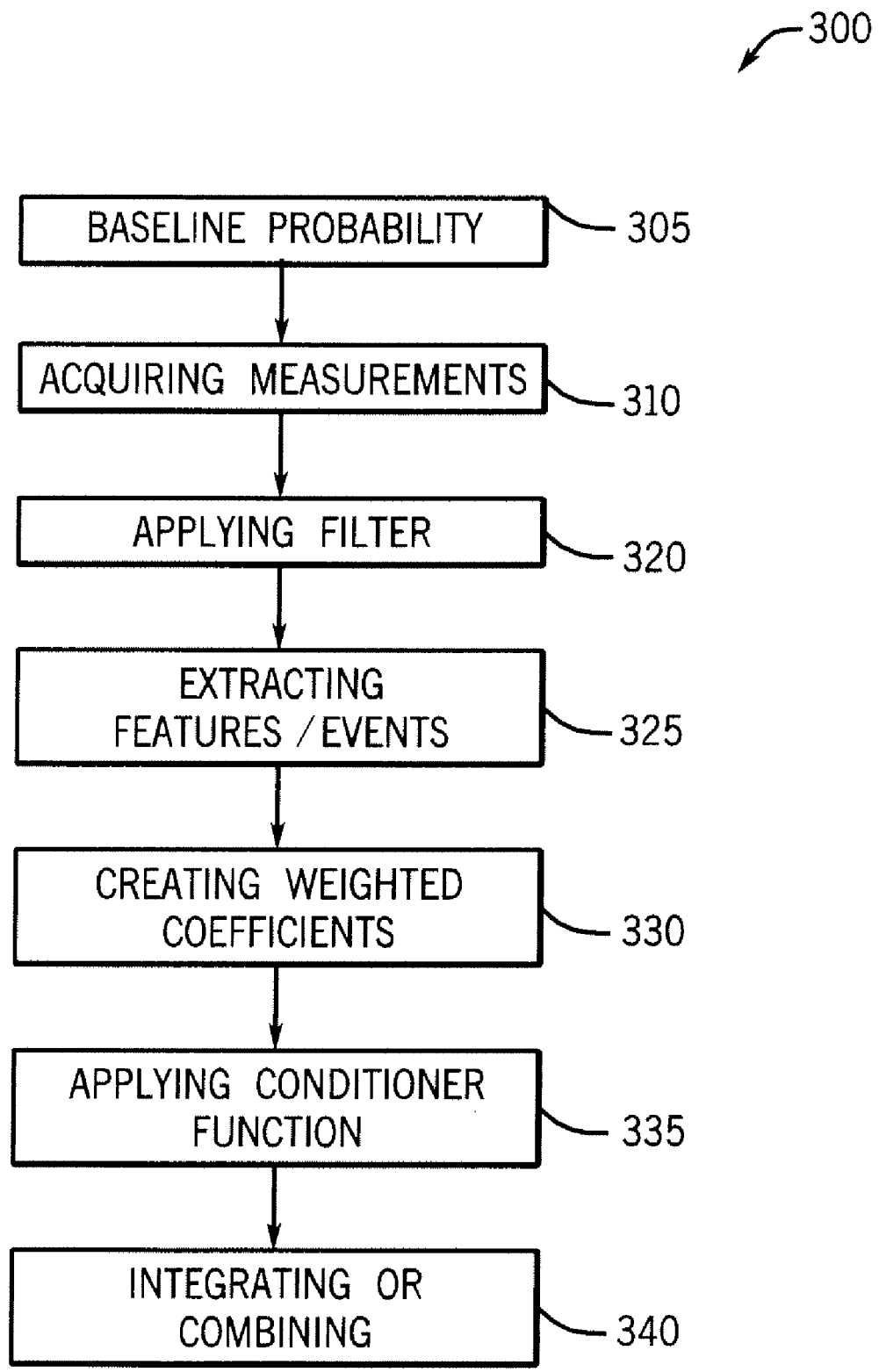
FIG. 3 includes a flow diagram illustrative of an embodiment of a method managing maintenance of the imaging system in FIG. 1.

FIG. 3 includes a flow diagram to illustrate an embodiment of a method 300 of operation of the system 100 in managing a maintenance of the radiation source 110. It should be understood that the sequence of the acts or steps of the method 300 as discussed in the foregoing description can vary. Also, it should be understood that the method 300 may not require each act or step in the foregoing description, or may include additional acts or steps not disclosed herein. It should also be understood that one or more of the steps of the method 300 can be represented as computer-readable program instructions in the memory 150 for execution by one or more processors of the controller 125 or remote computer. This method 300 can be modified or customized for each individual tube assembly 115 based on tracking of specific events and parametric or usage measurements.

One embodiment of the method 300 generally includes a step 305 of calculating or outputting an initial or baseline probability of failure or survivability, independent of machine condition or usage, such as by applying a reliability model. The step 305 can include acquiring input data and/or reliability models from one or more of a predetermined manufacturer's/engineering age-based reliability model, or on a reliability model created from acquired date across a population of machines.

One embodiment of the step 305 can include creating an algorithm or baseline model of a likelihood of or to predict a time to failure of the tube assembly 115. Based on a representative training sample dataset with known incidences of failure, step 305 can include identifying parameters of age and/or machine data and/or usage profile to be weighted as part of the baseline reliability model. One embodiment of the baseline reliability model can include mathematical function that provides a probability of survival of a component given the age of the component.

The baseline reliability model given the age of the component can include a weibull model whose parameters are estimated based on testing in design (e.g., HAST (Highly Accelerated Stress Test) or by observing population of the component in field. The baseline reliability model could also be a non-parametric model based on sample data from the observed population in field.

One embodiment of the baseline reliability model can be independent of usage of the tube assembly, radiation source, or system. Another embodiment of the baseline reliability model can be weighted by parameterized usage profile in a non-parametric reliability model framework such as Cox PH model wherein the hazard at time (t) can a function of baseline hazard using age ($h_0(t)$) which can be accelerated by the variables (X). The coefficients β can be weights assigned to different independent usage variables (X).

$$h(t)=h_0(t)\exp(X\beta) \quad (1)$$

An embodiment of the step 305 can include creating baseline reliability model to calculate the probability of survival of one or more components of the system 100 based on acquired data of an existing population of tube assemblies 115, such as represented by a Weibull distribution algorithm with defined parameters for shape and scale. Another embodiment of the step 305 of creating the baseline reliability model can be correlated to reliability test data acquired from the manufacturer. The baseline reliability model can be supplemented with weighted parameters for batch period information acquired to incorporate or represent variation in manufacturing.

Similar to the addition of usage parameters to the baseline reliability model described above, a variable for the manufacturing model/batch period information can be incorporated into the baseline reliability model. The batch variable can be incorporated as a categorical variable similar to variable (X) in the Cox-PH model described above. The batch variable can also be incorporated in the form of a stratified model; where each model period can have its own baseline reliability model with common values for the coefficients β assigned to usage.

Step 310 can include acquiring and applying measurements of additional parameters for application in one or more of the above-described models or algorithms (e.g., system usage model, component usage model, composite usage model) in step 305. The measured parameters can include machine data for one or more components or sub-systems, and usage at the radiological imaging level or component level of the radiation source 110 or tube assembly 115. For example, one embodiment of the measurement of parameters for application in the model can include continuous measurements directed to failure at the sub-system/component level (e.g., directed to failure prognostics of the tube assembly 115, data directed to the tube rotor 200, measurements of high voltage related failures, etc.).

The parameters represented in one or more of the above-described usage or composite models can represent measurement data of occurrence of discrete events, also referred to as event codes. The occurrence of event codes can include the occurrence of exceptions/error messages logged in the imaging system 100. Measuring these event codes can include acquiring feedback and detecting crossing of trend in data relative to pre-set threshold levels, occurrence or output of system state messages (e.g., abort of exam etc.) due to interaction with type of imaging scans performed, conditions of operation of the radiological imaging system or radiation source 110. The occurrence of these event codes may be discontinuous and noisy in nature.

Figure 4:
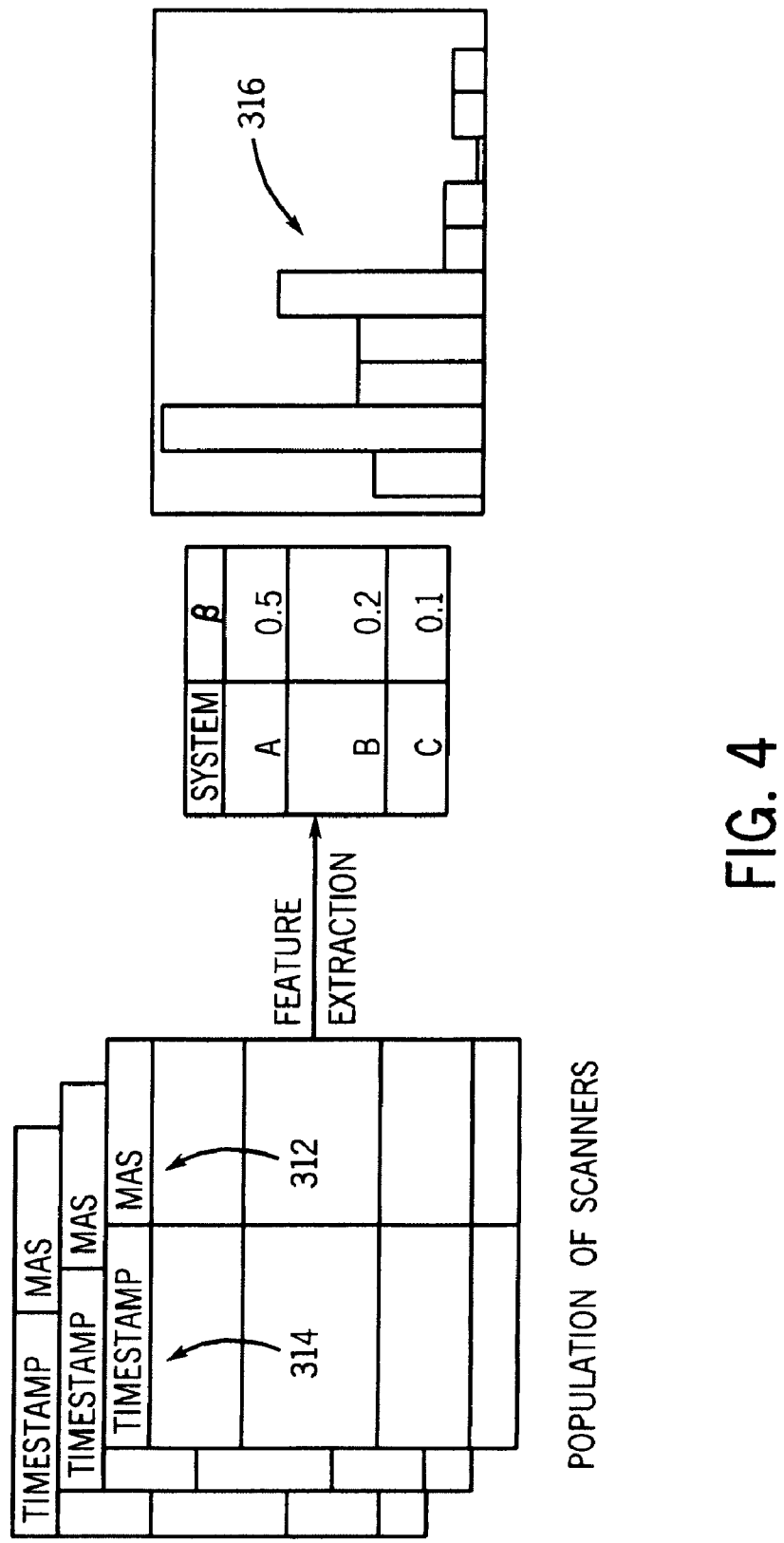
FIG. 4 includes a graphical representation of an embodiment of extraction of an occurrence of a feature or event code and creating a model of trend thereof in occurrence dependent on a histogram.

Step 310 can further include measuring or acquiring data of usage of the imaging system or radiation source 110 measured across different dimensions based on nature of the measurement and its relationship to the component. For example, the usage measurements can be broadly classified into the following categories: system usage parameters can include quantity and type of usage for the imaging system in general (e.g., number of scans/diagnostic images acquired over a period of time, a type of diagnostic exams performed (degree of mix of types of diagnostic exams performed by a given system, etc.). Referring to FIG. 4, usage parameter measurements can also include tracking or acquiring measurement of component usage-parameters which can be incremented based on some measure of usage specific to the component (e.g., milli-amp seconds (mAS) as referred to by reference 312 relative to a time stamp 314) of usage or operation of tube assembly 115 over life of tube assembly 115), and creating a model or algorithm (e.g., based on histogram and reference 316) representative the rate of mAS usage independent of time (e.g., mAS usage per tube assembly 115).

Figure 5:
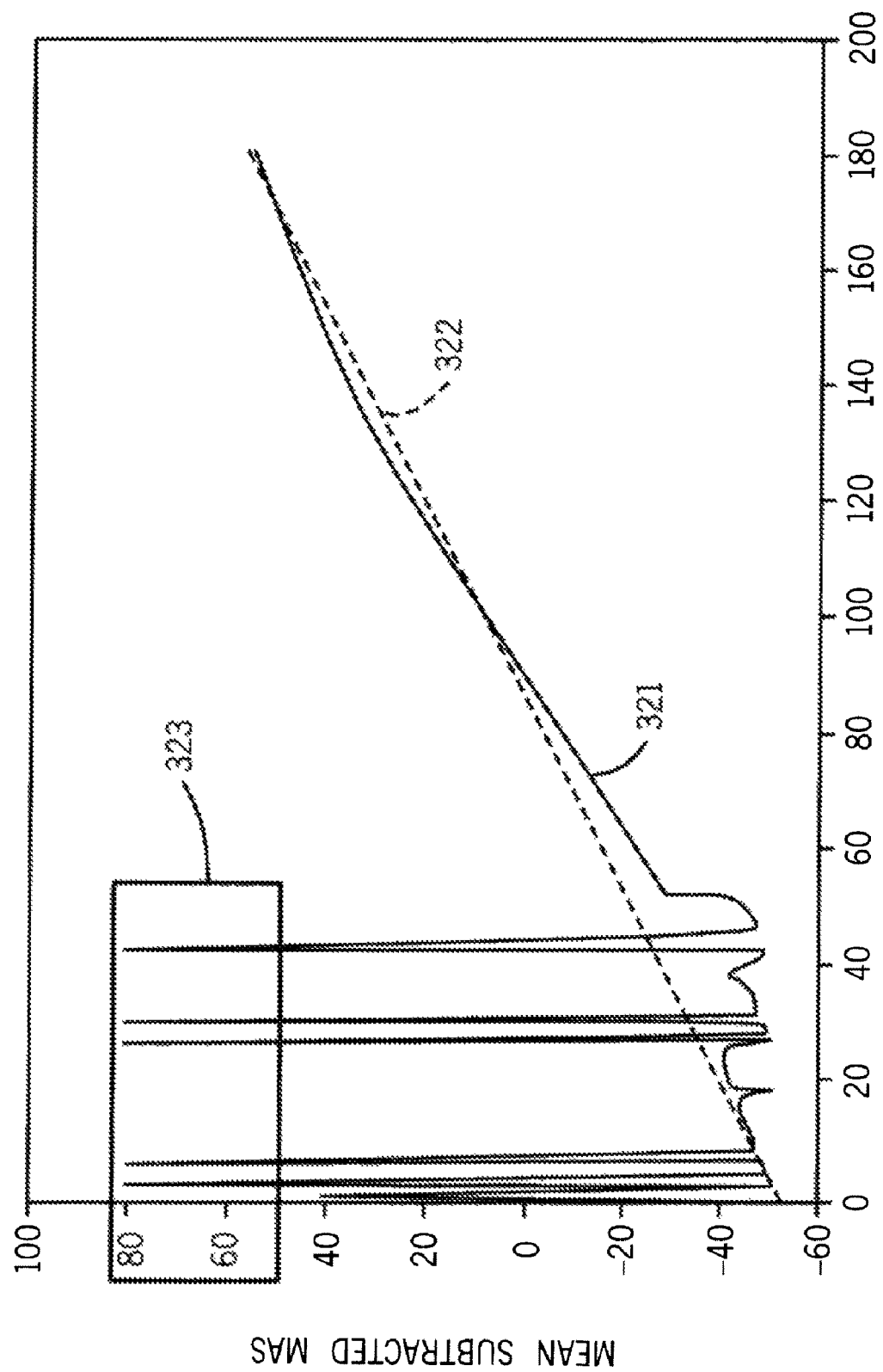
FIG. 5 includes a graphical illustration of a filter to acquired system or component level usage data, the filter generally operative to remove outlying data relative to a historical trend.

Step 320 can include applying a filter (also referred to as a "bad data filter") to remove outlying measurement data (relative to a threshold). Includes creating or developing a model or algorithm that defines or represents a baseline or continually measured/modified trend of usage f a feature (e.g., MaS records a measure of usage per tube). Referring to FIG. 5, step 320 in applying the filter can include calculating or acquiring a rate of usage (e.g., example of mAS usage illustrated as reference 321), comparing the acquired measured rate 321 relative to the trend model or algorithm 322, and calculating a departure from the trend model 322. A bad data filter can be operable to remove data categorized as large-scale single outliers (examples generally shown within frame and reference 323 of FIG. 5), which can be physically infeasible and therefore represent bad data. The bad data filter can remove or eliminate these large-scale single outliers 323, based on developed feature for new real-time data in production to improve robustness of system 100.

Step 325 can include extracting details of one or more features to improve dimension reduction and to extract relevant input data. An embodiment of the step 310 of measuring usage can cause or trigger the step 325 of extracting features, such as those independent of the age of the component and usage parameters. One embodiment of step 325 can include applying or executing feature extractions tools to both continuous and discrete (event) data. Feature extraction for parametric data can includes dimension reduction strategies (multivariate feature extraction: PCA; or time series feature extraction FFT; wavelet etc.). The discrete events (event codes) can be representative of a change in system states or certain measurements crossing predetermined threshold values. Typically a large number of such events are reported by the system (~2000 unique event). Events can be transient in nature or noisy (state of the event code can change frequently) due to interactions with other components/sub-systems and usage. Therefore feature extraction consists of selecting events related to failure modes of interest and the coefficient associated with each event in Eq. (1). This can be done in step 325 by acquiring or tracking a frequency of occurrence of each event code in a given time window as a feature corresponding to the event, based on an impact occurrence of an event code can decrease with time. Occurrences of the event code relative to a time window (e.g., 20 days) or individual occurrences can be weighted based on time of occurrence of the event code.

An embodiment of step 330 can include combining or integrating one or of the above-described usage algorithms with another (system or one or more component level algorithms) to create a composite or combined model or algorithm to calculate the survival probability of the system 100. For example, the step 330 can include acquiring measurements of both system level usage and component usage parameters to calculate or output a combined usage parameter value for integration in the usage algorithm. In another example, the usage parameters at the system level or component level may not be completely independent of each other. The step 330 can include calculating a composite usage of the system 100 that represents a weighted combination of one or more system level usage parameters (e.g., exam counts) with one or more of the component level usage-parameters (e.g., MAS/per component).

Figure 6:
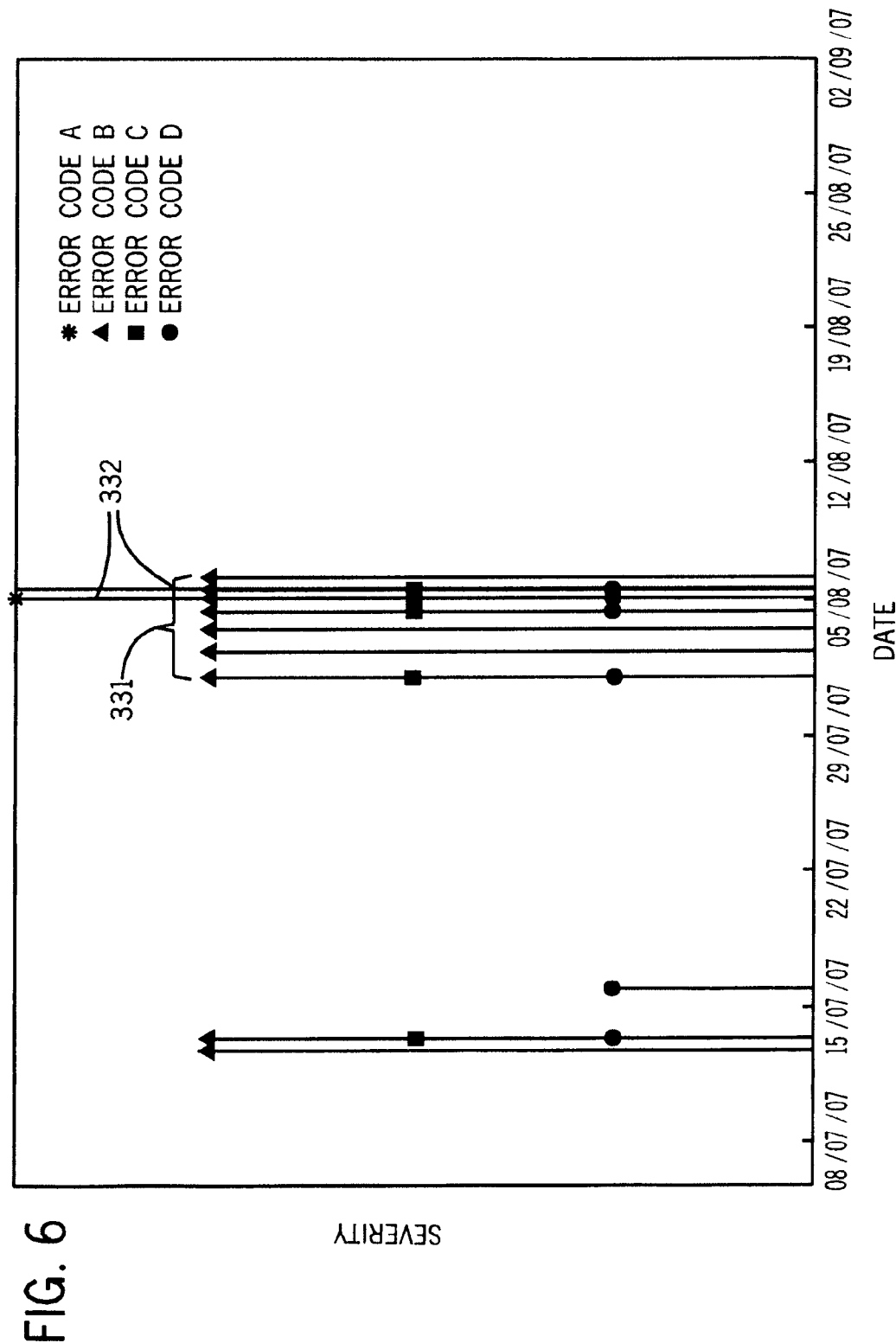
FIG. 6 includes a graphical illustration of a step of identifying significance of multiple error codes that can be applied in weighted relevance in combination with measurement of the usage parameters to calculate the probability of survivability of the system, radiation source, or tube assembly.

In another example, step 330 can include integrating or combining algorithms dependent on acquired usage as described above with one or more algorithms dependent on acquired data of event codes. Step 330 can include identifying multiple error codes as significant based on the analysis that can be applied in combination with measurement of the usage rate to the failure prediction model. For example in referring to FIG. 6, step 330 can include calculating significance of event codes in correlation or proportion to tracking of the number of occurrences (e.g., four different event codes and reference 331) at a sub-component of the rotor 200 in combination with the severity of occurrence (e.g., failure as shown by reference 332) of the sub-component of the rotor 200. The severity can be assigned predetermined weights or values and stored at the controller 125.

Step 330 can include assigning or calculating a weight to each measurement of component usage or parameters for error code features relative to one another. As individual parameters for error codes may not be independent of each other, the method 300 can include calculating a composite parameter generally equal to a weighted coefficient multiplied to the measurement of each individual error code parameter. Based on a representative training dataset sample of measurement of component failure event/feature parameters, the controller 125 can select or receive instructions to use the set of error codes related to the specific failure modes that are detected based on the ability of the measurement of the parameters of the error code features to differentiate between the system 100 with a failing tube (a tube with little remaining life) versus the system with a normal tube a tube with significant remaining life).

Of course, step 330 can include combining one or more aspects or portions of the algorithms described above with another and is not limiting on the technique described herein.

Step 335 includes applying a conditioner function. For example, based on the extracted features for parametric, event and usage parameters, the step 335 can include applying a conditioner function to adjust the reliability model so as to calculate a per-system calculation of survival probability. The conditioner function can be defined as a Bayesian type filter operable to modify the prior probability of failure given new information regarding system condition. A typical embodiment of the conditioner function is the exponential function.

An embodiment of step 335 can include acquiring a representative dataset sample (e.g. training) of component failures, creating a model or algorithm of the conditioner function after accounting for the reliability output according to the reliability algorithm. The conditioner function can comprise a selection of optimum set of features (from a series of tracked features) to be included in or applied to the reliability model based on the corresponding significance of weighted coefficients. An example of the model can calculate a reliability or probability of failure or survival of a tube assembly 115 based on training or calibration data for the system of interest for a condition of at least one of normal and failed radiation source 110 or tube assembly 115.

Step 340 includes integrating or combining the non-usage baseline reliability model with the reliability model based on usage data, parametric and feature extraction (e.g., error codes) to predict the survival or limited life remaining of the tube assembly 115. The individual coefficients (β) applied to one or more of the non-usage baseline reliability models/algorithms or parameters described above can be estimated based on sample population. The relationship between the non-usage baseline reliability model or parameters described above can be captured by interaction terms.

One or more parameters can be weighted by their respective coefficients, which are obtained from training historical data, are summed to form a combined feature, which is then input into the conditioner 445 (see FIG. 8) and further transformed into a number representing the risk of failure due to the exhibited operating feature of the tube assembly 115.

Figure 7:
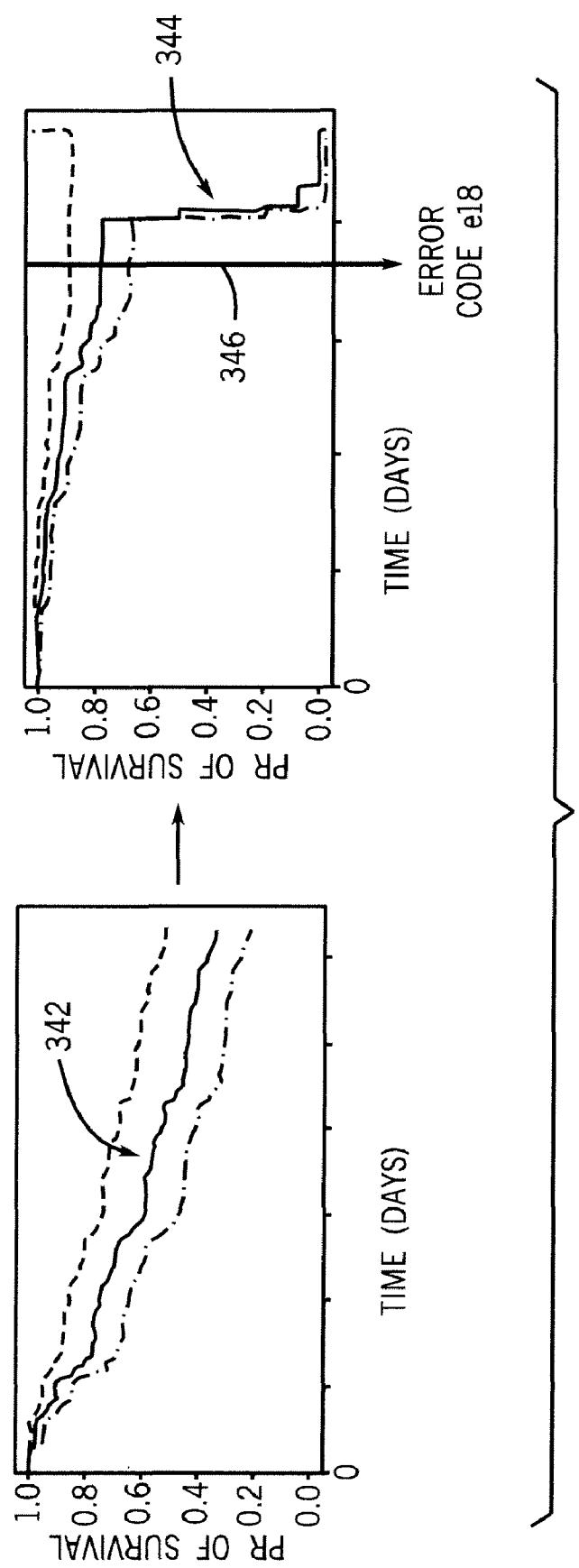
FIG. 7 includes a graphical illustration of an embodiment of the step of adjusting a baseline probability of survivability of the imaging system or tube assembly thereof dependent on acquired data of occurrence of event codes with respect thereto.

The integrated/combined model can be a weighted combination of the non-usage model in combination with the non-usage model. FIG. 7 shows an illustration of an example of calculation of probability of survival based on non-usage reliability model (e.g., age only) (see reference 342) that can be adjusted (see reference 344) to show a change in predicted reliability or failure or survivability dependent or changed in response to acquired measurements of error code (see reference 346) and usage parameters, combined with weighted coefficients as described above.

An embodiment of the step 340 of combining or integrating so as to create a combined or composite predictive algorithm or model to output the probability of failure or survival of the imaging system 105 (or radiation source 110 or tube assembly 115 thereof) at time (t) can be according to the following function:

$$p(t) = p_0(t) * fn(e18 + e19 + e53 + e48 + \text{usage\_unit})$$

where $p(t)$ represents probability at time (t), $p_0(t)$ represents a baseline probability value calculated from the baseline reliability algorithm described above, and e18, e19, e53, e48 represent weighted error code feature parameters, and usage_unit represents one or more parameters of usage described above selected for incorporation in the composite model to calculate the survival probability of the system 110 at time (t).

Figure 8:
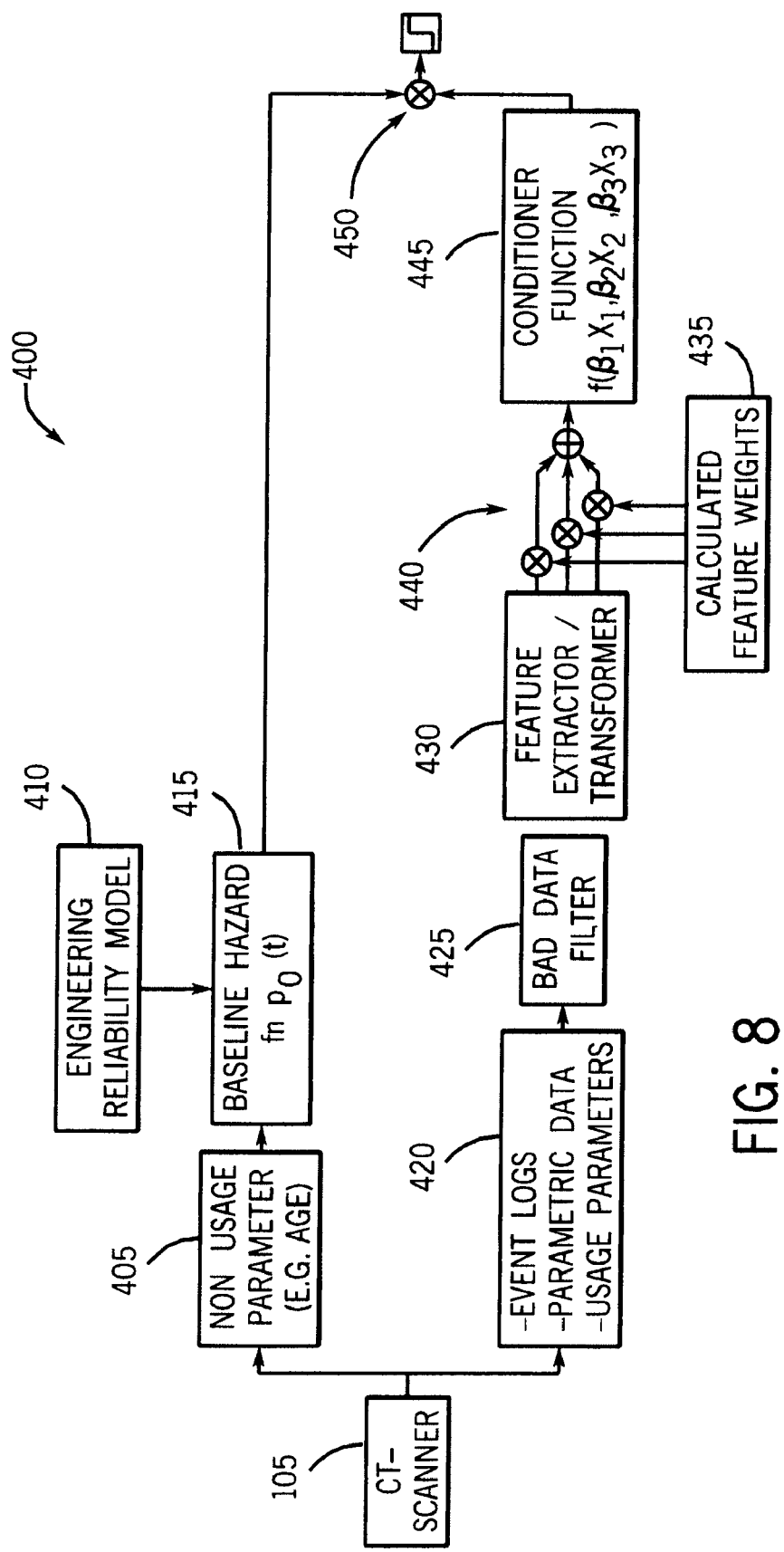
FIG. 8 illustrates a block diagram illustrative an embodiment of a software comprising a series of modules of program instructions operable to instruct a processor of the management system to perform the steps of managing the imaging system in accordance with the embodiment of the method of FIG. 3.

FIG. 8 illustrates an embodiment of a software or software package 400 that comprises a series of program modules of instructions that can be stored in the memory 155 for execution by the processor 150 of the controller 125. The embodiment of the series of program instructions of the software 400 generally correlate with the method 300 described above to manage and output the survivability of the imaging system 105. Module 405 generally includes program instructions to acquire data of non-usage parameters associated with the imaging system 105, either from the imaging system 105 or via the input 160. Module 410 generally includes program instructions to acquire a baseline reliability algorithm(s) and data from at least one of the manufacturer of the imaging system 105 or radiation source 110 thereof, or to acquire a dataset or algorithm from a compilation acquired from a population of other imaging systems independent of the imaging system 105 or radiation source 110 of interest. Module 415 generally includes program instructions directed to applying the acquired output from at least one or both of the modules 405 and 410 in calculating or creating an output of the baseline probability of the failure or survivability of the system 105 or the radiation source 110 or tube assembly 115 thereof.

Module 420 generally includes program instructions to acquire measurements of logs or occurrences of event codes, usage data, or other parameter metrics associated with operation of the imaging system 105 or the radiation 110 or tube assembly 115 thereof. Module 425 generally includes program instructions to filter bad data before application in the algorithm to predict failure or survivability of the imaging system 105 or radiation source 110 or tube assembly 115 thereof, similar to step 320. Module 430 generally includes program instructions to extract or transform features from the output acquired from the module 425. An example of module 430 in extracting the feature can include instructions to calculate or measure the frequency of occurrence of each event code in a given or acquired time window which may correspond to an event, or measure a change of an impact of an occurrence of an event code with time, etc. Module 435 generally includes program instructions to calculate or adjust weighted coefficients to be applied to the above-described parameters comprising the algorithm 440 in calculating the failure or survivability of the imaging system 105 or radiation source 110 or tube assembly 115 thereof.

Module 445 generally includes program instructions to apply a conditioner function as described in step 335. Module 450 includes instructions to combine or integrate the output of the baseline reliability or probability algorithm with operating parameter algorithms/models so as calculate probability of time period to failure or survivability of the system 105 or radiation source 110 or tube assembly 115 thereof, as described in step 340.

Having provided the above-described description of the embodiment of the system 100 and method 300 and the above-mentioned baseline probability algorithm and conditioner function algorithm, the following is a description of an example of executing the method 300 or software 400 with the system 100 in managing the survivability of the imaging system 105 or the radiation source 110 or tube assembly 115 thereof.

Assume a given time ($t_0$) and acquiring the age of the radiation source 110 or tube assembly 115 at time ($t_0$), the controller can calculate the baseline probability of survival of the component for any time ($t_0 < t < t_1$); where ($t_1 - t_0$) is the acquired or preset prediction horizon or prediction interval forward from the present.

The module 445 of the conditioning function can modify or adjust acquired data or output of the usage based reliability model based on the usage and data acquired of the error code features extracted until time $t_0$, and the estimated usage feature values until $t_1$. A pre-set threshold can be determined for survival probability for which a trigger can be generated to inform the service operations to service/replace the component, e.g., a survival probability of 0.05 can be considered as the threshold to replace/service the tube. Alternatively, the estimated time to failure from the accelerated reliability model can be used in conjunction with the time required to service the component to generate the trigger, e.g., if the time to failure is estimated to be 3 days and the time to repair the component is 2 days a trigger may be generated to allow sufficient time to service the component without causing downtime.

The above provides a description of embodiment of the system 100 and method 300 to predict a failure of an imaging system 105 that includes an x-ray tube assembly 115 as a radiation source 110. The embodiment of the method 300 can comprise the steps of acquiring an age of the x-ray tube assembly 115; calculating a baseline probability of a survivability of the tube assembly 115 for a remaining time period independent of a usage of the tube assembly 115; acquiring measurement of at least one operating parameter of the x-ray tube assembly 115; and automatically changing the probability of a survivability of the x-ray tube assembly 115 in response to the measurement of the at least one operating parameter of the x-ray tube assembly 115. An embodiment of the at least one operating parameter can include a measure of a severity of an occurrence of an event code generated by the imaging system 105, the event code associated with an abnormal operating condition of the radiation source 110. An embodiment of measurement of the at least one operating parameter can include measurement of a frequency of an occurrence of an event code generated by the imaging system 105, or the event code associated with an abnormal operating condition of the radiation source 110. The method 300 can further include the step of extracting the event code from acquired data received from the imaging system 105, the event code representative of at least one of: an error message, a measurement outside of a threshold range, and a message indicative of a state of the imaging system 105. An embodiment of the baseline probability of the survivability of the system 105 can be dependent on acquired data of a survivability for a population of other x-ray tube assemblies 115 with age and usage of the imaging system 105. An embodiment of the at least one operating parameter can generally equal a measure of usage of imaging system 105 weighted relative to a measure of an occurrence of event codes associated with operation of the imaging system 105, or the at least one operating parameter can generally equal a measure of usage of the imaging system 105 weighted relative to a measure of usage of the tube assembly 115 of the system 105 independently thereof. An embodiment of the step of automatically changing the baseline probability of time to failure of the imaging system 105 can include decreasing the probability survivability of the imaging system 105 in response to acquiring a measurement of an occurrence of an event code outside a threshold range, or can include decreasing the probability survivability in proportion to a predicted value of usage of one or more of the imaging system 105, the radiation source 110, and the tube assembly 115.

According to the embodiment of the system 100 to predict a failure of the imaging system 105 that includes the radiation source 110 having the x-ray tube assembly 115, the system 100 can comprise a storage medium having a plurality of programmable storage instructions; and a processor in communication with the imaging system, the plurality of program instructions to instruct the processor to perform the steps of: acquiring an age of the x-ray tube assembly 115, calculating a baseline probability of a survivability of the tube assembly for a remaining time period dependent on the age of the tube assembly, acquiring measurement of at least one operating parameter of the x-ray tube assembly, and automatically changing the baseline probability of a survivability of the imaging system for the remaining time period in response to the measurement of the at least one operating parameter of the x-ray tube assembly. The system of claim 10, wherein the at least one operating parameter includes a measure of a severity of an occurrence of an event code generated by the imaging system, the event code associated with an abnormal operating condition of the radiation source, or a measure of usage of the x-ray tube assembly. The system of claim 10, wherein measurement of the at least one operating parameter includes measurement of a frequency of an occurrence of an event code generated by the imaging system, the event code associated with an abnormal operating condition of the radiation source. The system of claim 10, further comprising the step of extracting the event code from acquired data received from the imaging system, the event code representative of at least one of: an error message, a measurement outside of a threshold range, and a message indicative of a state of the system. The system of claim 10, the baseline probability of the survivability of the system is dependent on acquired data of a survivability for a population of other x-ray tube assemblies with age and usage of the imaging system. The system of claim 10, wherein the at least one operating parameter generally equals a measure of usage of imaging system weighted relative to a measure of an occurrence of event codes associated with operation of the imaging system. The system of claim 10, wherein the at least one operating parameter generally equals a measure of usage of the imaging system weighted relative to a measure of usage of the tube assembly of the system independently thereof. The system of claim 10, wherein the step of automatically changing the baseline probability of time to failure of the imaging system includes decreasing the probability survivability of the imaging system in response to acquiring a measurement of an occurrence of an event code outside a threshold range. The system of claim 10, wherein the step of automatically changing the baseline probability of time to failure of the imaging system includes decreasing the probability survivability in proportion to a predicted value of usage of one or more of the imaging system, the radiation source, and the tube assembly. The system of claim 10, wherein the baseline probability of a survivability of the imaging system for the remaining time period includes a predicted number of hours or days to failure.

A technical effect of the above-described system 100 and method 300 includes combining machine data with reliability model and usage profile to provide higher accuracy for the failure prediction, as well as high accuracy prediction of minimum remaining life so as to reduce cost of proactive replacement. The accuracy of the prediction to failure can depend on the time frame or horizon for the failure prediction, and the nature of prediction (prediction of failure of individual components versus prediction of failure of the system 105 or components of fleet of systems). A first example is directed to failure prediction of a component that is system specific and having a short-term prediction horizon or time frame, and based on measured or acquired data of machine event codes and usage. The system 100 and method 300 can combine the reliability model with machine event codes and usage data for a specific system. Further, given similar conditions for the system in terms of age of the tube and occurrence of error codes/parametric values, the system 100 can predict the probability of survival for the component in the required time window (e.g., 30 days) based on the modeled usage profile for the imaging system 105. The system 100 and method 300 can be automatically updated based on new data sent by the system to update parametric/error and usage features, and can acquire updated values to provide a new estimate of time to failure and the confidence intervals for the same. The system 100 and method 300 can also integrate the failure prediction with business and logistics inputs in terms of transportation time (based on distance of the hospital to depot), cost of downtime to the hospital, the model can be used to determine optimum trigger for service of component. These inputs can be used as additions to the constraints outlined above in terms of accuracy and TTF requirements in the model for optimum prediction.

The system 100 and method 300 can also be used to predict the number of failures of tubes for a given time period in a given geographical area. The outputs of the system 100 and method 300 can enhance predictions of survival of components and/or system 105 by combining output from the reliability model with acquired data of usage patterns for individual systems 105 or assemblies 115. The system 100 and method 300 can be scaled to the required prediction horizon or time frame (e.g. 4 months) and for a group of components or systems 105. The length of prediction horizon and grouping of systems 105 can be determined based on geographical zones and horizon for inventory planning. The proposed system 100 can then use the probability of failures for each individual system 105 (based on its age and usage characteristics) to provide a stochastic estimate of expected number of tube failures in the geographical area for given time frame. This would provide a more accurate estimation than deterministic estimation of failures of tube assemblies 115 based on age alone.

Another technical effect of the above-described system 100 and method 300 includes providing robust failure prediction and sufficient time to failure to prevent downtime by proactive service. Further the prediction is based on the modeling the usage profile that allows for leaving minimum remaining life at prediction, since it conditions the time to failure based on predicted usage of the component. The ability to perform failure prediction, e.g., for tube assemblies 115 for example in CT imaging systems 105 can provide significant benefit to customer in terms of reduced downtime and the focus of the proposed methodology can be able to predict (e.g., at least 2 days) before failure. Further, the ability to predict tube failure allows for savings per tube requiring special handling. Also, the system 100 and method 300 can calculate a minimum remaining life on the tube assembly 115 as the cost of each day of remaining life on a tube assembly 115. Another technical effect of the system 100 and method 300, given the large scale of the install base and the number of expected failures of x-ray tube assemblies 115 per year, provides for accurate prediction of failures of tube assemblies 115 based on geographical area. This can help both ensuring availability of tube assemblies 115 in the closest depot for the imaging system 105 having a failure of the tube assembly 115 and also help in reducing inventory holding cost.

This written description uses examples to disclose the subject matter, including the best mode, and also to enable one skilled in the art to make and use the invention. The patentable scope of the subject matter is defined by the following claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

We claim:

1. A method (300) to predict a failure of an imaging system (105) that includes an x-ray tube assembly (115) as a radiation source (110), the method (300) comprising:
    acquiring an age of the x-ray tube assembly (115);
    calculating a baseline probability of a survivability of the tube assembly (115) for a remaining time period independent of a usage of the tube assembly (115);
    acquiring measurement of at least one operating parameter of the x-ray tube assembly (115);
    applying a filter to the acquired measurement, the filter configured to remove outlying measurement data representing a deviation from a trend model and modify the measured at least one operating parameter to remove the outlying measurement data;
    acquiring usage data of the imaging system including a type and quantity of images acquired over time;
    predicting a usage of the x-ray tube assembly based on the acquired usage data; and
    automatically changing the probability of a survivability of the x-ray tube assembly (115) in response to the modified measurement of the at least one operating parameter of the x-ray tube assembly (115) and the predicted usage.

2. The method (300) of claim 1, wherein the at least one operating parameter includes a measure of a severity of an occurrence of an event code generated by the imaging system (105), the event code associated with an abnormal operating condition of the radiation source (110).

3. The method (300) of claim 1, wherein measurement of the at least one operating parameter includes measurement of a frequency of an occurrence of an event code generated by the imaging system (105), the event code associated with an abnormal operating condition of the radiation source (110).

4. The method (300) of claim 1, further comprising the step of extracting the event code from acquired data received from the imaging system (105), the event code representative of at least one of: an error message, a measurement outside of a threshold range, and a message indicative of a state of the system (105).

5. The method (300) of claim 1, the baseline probability of the survivability of the system (105) is dependent on acquired data of a survivability for a population of other x-ray tube assemblies with age and usage of the imaging system (105).

6. The method of claim 1 wherein applying the filter further comprises:
    calculating a rate of usage of the x-ray tube assembly;
    comparing the calculated rate of usage of the x-ray tube assembly to a usage trend model;
    calculating a departure of the calculated rate of usage from the usage trend mode; and
    modifying the measured at least one operating parameter to remove data falling outside of a pre-determined deviation from the calculated departure.

7. The method of claim 6 wherein the removed data comprises large-scale single outliers.

8. The method of claim 1 wherein changing the probability of survival further comprises comparing a predicted time to failure to a service event parameter and generating a trigger at a time corresponding to a predetermined service interval in advance of the predicted time to failure.

9. A system (100) to predict a failure of an imaging system (105) that includes a radiation source (110) having an x-ray tube assembly (115), the system (100) comprising:
    a storage medium (155) having a plurality of programmable storage instructions; and
    a processor (150) in communication with the imaging system (105), the plurality of program instructions to instruct the processor (150) to perform the steps of:
    acquiring an age of the x-ray tube assembly (115);
    calculating a baseline probability of a survivability of the tube assembly (115) for a remaining time period dependent on the age of the tube assembly (115);
    acquiring measurement of at least one operating parameter of the x-ray tube assembly (115);
    applying a filter to the acquired measurement, the filter configured to remove outlying measurement data representing a deviation from a trend model and modify the measured at least one operating parameter to remove the outlying measurement data;
    acquiring usage data of the imaging system including a type and quantity of images acquired over time;
    predicting a usage of the x-ray tube assembly based on the acquired usage data; and
    automatically changing the baseline probability of a survivability of the imaging system (105) for the remaining time period in response to the modified measurement of the at least one operating parameter and predicted usage of the x-ray tube assembly (115).

10. The system (100) of claim 9, wherein the at least one operating parameter includes a measure of a severity of an occurrence of an event code generated by the imaging system (105), the event code associated with an abnormal operating condition of the radiation source (110), or a measure of usage of the x-ray tube assembly (115).

11. The system (100) of claim 9, wherein measurement of the at least one operating parameter includes measurement of a frequency of an occurrence of an event code generated by the imaging system (105), the event code associated with an abnormal operating condition of the radiation source (110).

12. The system (100) of claim 9, further comprising the step of extracting the event code from acquired data received from the imaging system (105), the event code representative of at least one of: an error message, a measurement outside of a threshold range, and a message indicative of a state of the system (105).

13. The system (100) of claim 9, the baseline probability of the survivability of the system (105) is dependent on acquired data of a survivability for a population of other x- ray tube assemblies with age and usage of the imaging system (105).

14. The system (100) of claim 9, wherein the at least one operating parameter generally equals a measure of usage of imaging system (105) weighted relative to a measure of an occurrence of event codes associated with operation of the imaging system (105).

15. The system (100) of claim 9, wherein the at least one operating parameter generally equals a measure of usage of the imaging system (105) weighted relative to a measure of usage of the tube assembly (115) of the system (105) independently thereof.

16. The system (100) of claim 9, wherein the step of automatically changing the baseline probability of time to failure of the imaging system (105) includes decreasing the probability survivability of the imaging system (105) in response to acquiring a measurement of an occurrence of an event code outside a threshold range.

17. The system (100) of claim 9, wherein the step of automatically changing the baseline probability of time to failure of the imaging system (105) includes decreasing the probability survivability in proportion to a predicted value of usage of one or more of the imaging system (105), the radiation source (110), and the tube assembly (115).

18. The system (100) of claim 9, wherein the baseline probability of a survivability of the imaging system (105) for the remaining time period includes a predicted number of hours or days to failure.

* * * * *